United States Patent
Kummer et al.

[19]

[11] Patent Number: 5,851,209
[45] Date of Patent: Dec. 22, 1998

[54] BONE CERCLAGE TOOL

[75] Inventors: Frederick J. Kummer; Kenneth Koval, both of New York, N.Y.

[73] Assignee: Hospital for Joint Diseases, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 586,228

[22] Filed: Jan. 16, 1996

[51] Int. Cl.$^6$ ...................................................... A61B 17/56
[52] U.S. Cl. ............................................................. 606/103
[58] Field of Search .................................. 606/74, 60, 72, 606/86, 80, 79, 82, 83, 84, 85, 103, 139, 148, 149, 150, 170, 205, 222

[56] References Cited

U.S. PATENT DOCUMENTS

| | | |
|---|---|---|
| 1,346,940 | 7/1920 | Collins . |
| 2,049,361 | 7/1936 | Ericsson . |
| 2,301,500 | 11/1942 | Anderson . |
| 2,897,820 | 8/1959 | Tauber . |
| 3,037,619 | 6/1962 | Stevans . |
| 3,577,601 | 5/1971 | Mariani et al. . |
| 3,946,740 | 3/1976 | Bassett . |
| 4,441,497 | 4/1984 | Paudler . |
| 4,557,259 | 12/1985 | Wu . |
| 4,602,636 | 7/1986 | Noiles . |
| 4,606,335 | 8/1986 | Wedeen . |
| 4,622,960 | 11/1986 | Tam . |
| 4,625,717 | 12/1986 | Covitz . |
| 4,643,178 | 2/1987 | Nastari et al. . |
| 4,898,156 | 2/1990 | Gatturna et al. . |
| 4,901,727 | 2/1990 | Goodwin . |
| 4,935,027 | 6/1990 | Yoon . |
| 4,946,462 | 8/1990 | Watanabe . |
| 4,966,143 | 10/1990 | Meinershagen . |
| 4,976,684 | 12/1990 | Broadnax, Jr. . |
| 5,002,563 | 3/1991 | Pyka et al. . |
| 5,100,417 | 3/1992 | Cerier et al. . |
| 5,139,500 | 8/1992 | Schwartz . |
| 5,152,766 | 10/1992 | Kirkley . |
| 5,234,435 | 8/1993 | Seagrave, Jr. . |
| 5,250,055 | 10/1993 | Moore et al. . |
| 5,342,374 | 8/1994 | Wan et al. . |
| 5,350,385 | 9/1994 | Christy . |
| 5,387,221 | 2/1995 | Bisgaard . |
| 5,395,374 | 3/1995 | Miller et al. . |
| 5,431,658 | 7/1995 | Moskovich . |
| 5,439,467 | 8/1995 | Benderev et al. . |

*Primary Examiner*—Guy V. Tucker
*Attorney, Agent, or Firm*—Stephen E. Feldman, P.C.

[57] ABSTRACT

A bone cerclage tool for conformally slidably abutting a device circumferentially about a bone, such that orthopedic surgical procedures can be performed on and/or in the vicinity of the bone with minimal access and/or visibility and satisfying the need for complex maneuvering around anatomical parts and minimizing unnecessary tissue removal and contact with delicate areas. The bone cerclage tool can be used to encircle a bone with a suture, wire, cable, band, or device, to secure the bone in place, or perform operations on the bone or in the vicinity of the bone. The bone cerclage tool has a resilient member housed within a curved tube for guiding a device adjoined to the resilient member circumferentially about the bone and an exit section for directing the device to conformally slidably abut against the bone as the device is extended from the exit section. A push-pull member housed within a tubular housing and adjoined to the resilient member is used to extend or retract the device.

12 Claims, 3 Drawing Sheets

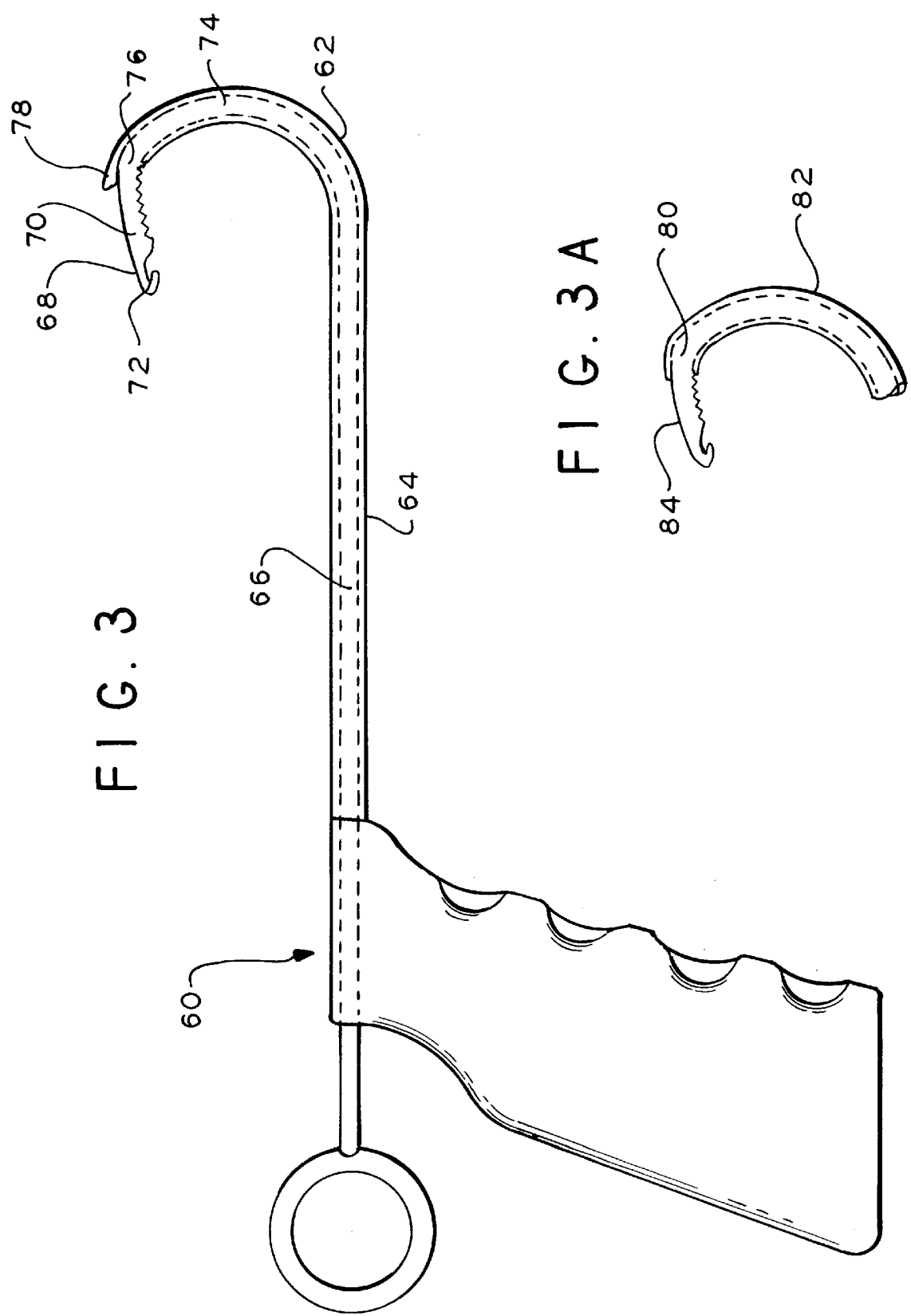

BONE CERCLAGE TOOL

BACKGROUND OF THE INVENTION

1. Field of the Invention

The present invention relates generally to surgical devices, and more particularly to an instrument to facilitate bone cerclage or pass wire or suture.

2. Background Art

Passing a wire, suture, wire saw, or other similar device around a bone during orthopedic procedures is a common surgical practice. The difficulty is to perform such procedures accurately, minimize complications, with minimum stress, trauma, risk, and injury to a patient, and with little difficulty for a surgeon performing such procedures, in as rapid a time frame as possible.

Surgical procedures on and in the vicinity of a bone with closely neighboring nerves, arteries, muscle, ligaments, complicated anatomical structures, and delicate areas represent a significant and difficult challenge to and time consuming task for the surgeon. Performing surgical procedures under, around, and through difficult to reach locations, apertures, and tunnels is in many instances an almost impossible task to the surgeon, given the need to minimize impact to the patient. Such tasks are complicated by the need to avoid damage to neighboring areas and minimize cutting away tissue to gain access to the area in which the surgical procedure is to be performed.

Small incisions, apertures, and tunnels are often necessary to minimize damage to and removal of surrounding tissue, nerves, arteries, muscle tissue, and delicate areas, in order to minimize stress, injury, risk, and trauma to the patient, and obviate the need for prolonged hospitalization and rehabilitation. The difficulty is compounded, while performing surgical procedures in deep surgical apertures or body cavities, in confined areas, and in situations requiring "endoscopic" or "closed" surgery and "microsurgery", requiring access to difficult to reach portions of the patient's body through small openings leading to the surgical site. It is further required to minimize the patient's time under anesthesia, in order to minimize certain deleterious effects of prolonged exposure to such anesthesia. Retrieval of the end of a suture or wire and resultant "fishing" for the suture or wire is often a problem, and time consumed in locating a device at a desired but difficult to reach location for a particular surgical procedure, delays surgery, becomes tedious to the surgeon, increases potential for error, complicates procedures, and prolongs the patient's exposure to anesthesia.

In many instances, the situation is complicated, when complex maneuvering is required around anatomical parts. It is often necessary to encircle a bone with a suture, wire, cable, band, or device, to secure the bone in place; repair a bone fracture or attach an appliance to the bone; or perform operations on the bone or in the vicinity of the bone, while only having minimal access and/or visibility to an area. Placement of the suture, wire, cable, band, or device through small openings, around tight, blind corners, without damaging nerves, arteries, and muscle tissue then becomes a tedious and complicated operation.

It is highly desirable to minimize the amount of tissue removal; not to disturb, cut, or push away tissue; and minimize contact with delicate areas and impact to the patient, while performing surgical orthopedic procedures, that could otherwise be accomplished by only passing a suture, wire, cable, band, or device around the bone, if a suitable tool would be available.

Different surgical tools have heretofore been known. However, none of the tools adequately satisfies these aforementioned needs. U.S. Pat. No. 1,346,940 (Collins) discloses an apparatus for binding fractured bones with a metallic band, comprising a plate like finger with attached metallic band pivoted by screws within the ends of a fork. U.S. Pat. No. 2,049,361 (Ericcson) describes a wire or ribbon tightening apparatus, having a clamping device, an aperture member, and moving flange for twisting and tightening a wire around a bone. U.S. Pat. No. 3,037,619 (Stevans) discloses a suture device with a suture material crimper at the end of a needle with the suture material contained in a tube, for use by a physician in making an emergency suture. U.S. Pat. No. 4,898,156 (Gatturna et al) relates to a plunger driven suture anchor for attaching objects to a bone, by anchoring one end of a suture in the bone and leaving the other end of the suture for attaching to the desired object. U.S. Pat. No. 4,935,027 (Yoon) discloses continuous feeding of suture material through a jaw member. U.S. Pat. No. 5,002,563 (Pyka et al.) relates to sutures that utilize shaped memory alloys, which may be placed in a stiff sleeve during insertion. U.S. Pat. No. 5,350,385 (Christy) discloses a surgical incision closure device, which is shaped in an elongated "J". U.S. Pat. No. 5,387,221 (Bisgaard) relates to a needle driving device comprising a needle holder for a curved suturing needle, the needle being driven from the needle holder by a rod, which is flexible at the foremost end. U.S. Pat. No. 5,439,467 (Benderev et al.) describes a suture passer with a handle and an elongate tubular probe guide, which may be straight or curved. Most of the surgical tools heretofore known have a fixed curvature, requiring large exposure and tunneling around and behind the bone and without accomplishing complete cerclage of the bone.

For the foregoing reasons, there is a need for a bone cerclage tool that can be used to perform orthopedic procedures accurately, encircle a bone with a suture, wire, cable, band, or device, to secure the bone in place, or perform operations on the bone or in the vicinity of the bone, while only having minimal access and/or visibility to an area and satisfying the need for complex maneuvering around anatomical parts, minimize complications, tissue removal, contact with delicate areas, and with minimum stress, trauma, risk, and injury to a patient, with little tedium to and as rapidly as possible by a surgeon performing such procedures.

SUMMARY

The present invention is directed to a bone cerclage tool that satisfies the needs for a surgical device that can be used to encircle a bone with a suture, wire, cable, band, or device, to secure the bone in place, or perform operations on the bone or in the vicinity of the bone, while only having minimal access and/or visibility to an area and satisfying the need for complex maneuvering around anatomical parts. The present invention minimizes complications and the need for unnecessary tissue removal and contact with delicate areas. Placement of a suture, wire, cable, band, or device through small openings, around tight, blind corners, without damaging nerves, arteries, muscle tissue is now possible with the present invention, and surgical orthopedic procedures can be performed with improved accuracy, minimum stress, trauma, risk, and injury to a patient, and little tedium to and as rapidly as possible by a surgeon performing such procedures.

A bone cerclage tool having features of the present invention comprises: a resilient member having a most distal end configured with a device for conformally slidably abutting circumferentially about a bone and for performing operations on and around the vicinity of the bone, the resilient member housed within a curved tube for guiding the resilient member circumferentially about the bone, the curved tube having a section with an exit for directing the device at the distal end of the resilient member to conformally slidably abut against the bone as the resilient member and the device at the distal end of the resilient member are extended from the exit section; a push-pull member adjoined to the resilient member for pushing and pulling the resilient member, such that the resilient member and the device are extended from the exit section when the push-pull member is pushed and retracted towards the exit section when the push-pull member is pulled; means for gripping the push-pull member; a tube adjoined to the curved tube for housing the push-pull member; and means for holding the bone cerclage tool.

The device at the distal end of the resilient member of the bone cerclage tool may be configured with: a hook for pulling the suture, wire, cable, or band around the bone; a saw for cutting the bone; a drill, router, screw driver, knife, or needle; means for grasping an object, such as spring fingers; or another appropriate implement for performing operations on or in the vicinity of the bone. The curved tube of the present invention may further comprise: a bendable semi-rigid material for conformally shaping the curved tube to the bone, allowing complex maneuvering around anatomical parts and different size bones. Additionally, the exit section of the present invention may have an internal diverter, or the exit section may be directed obliquely from the curved tube, for directing the resilient member and the device at the distal end of the resilient member obliquely from the curved tube, and for directing the device to conformally and proximately slidably abut against the bone.

DRAWINGS

These and other features, aspects, and advantages of the present invention will become better understood with regard to the following description, appended claims, and accompanying drawings where:

FIG. 3 is a side view of a bone cerclage tool which is another embodiment of the present invention; and FIG. 3A is a side view of an alternative exit section arrangement of the bone cerclage tool of FIG. 3.

DESCRIPTION

Figure 1:
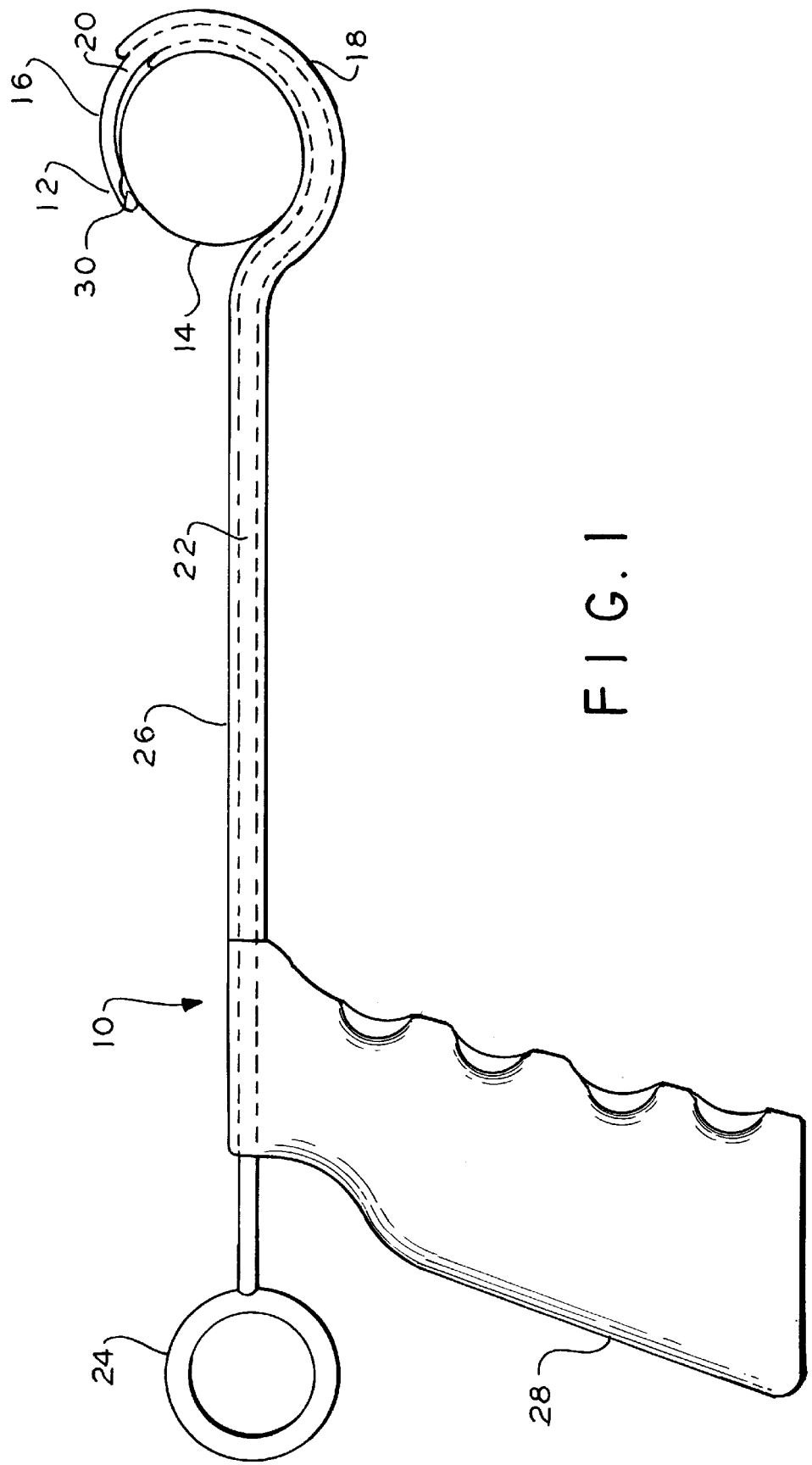
FIG. 1 is a side view of a bone cerclage tool which is one embodiment of the present invention.

FIG. 1 shows an embodiment of the invention, a bone cerclage tool 10 for conformally slidably abutting a device 12 circumferentially about a bone 14, such that orthopedic surgical procedures can be performed on and/or in the vicinity of the bone 14 with minimal access and/or visibility and satisfying the need for complex maneuvering around anatomical parts and minimizing unnecessary tissue removal and contact with delicate areas. The bone cerclage tool 10, has a resilient member 16 for conformally slidably abutting the device 12 adjoined to the resilient member 16 circumferentially about the bone 14. The resilient member 16 is housed within an arcuate tube 18 for guiding the resilient member 16 circumferentially about the bone 14. The arcuate tube 18 has an exit 20 for directing the device 12 to conformally slidably abut against the bone 14, as the device 12 is extended from the arcuate tube 18. A push-pull member 22 is adjoined to the resilient member 16 for pushing and pulling the resilient member 16, such that the resilient member 16 and the device 12 are extended from the exit 20 when the push-pull member 22 is pushed and such that the resilient member 16 and the device 12 are retracted towards the exit 20 when the push-pull member 22 is pulled. A ring shaped handle 24 is provided for gripping the push-pull member 22. A tube 26 is adjoined to the arcuate tube 18 for housing the push-pull member 22, and a pistol grip handle 28 is provided for holding the bone cerclage tool 10.

During surgical procedures the area in and around the vicinity of the bone 14 is prepared, and the arcuate tube 18 of the bone cerclage tool 10 is slidably abutted against the bone 14 with the device 12 retracted toward the exit 20. After the bone cerclage tool 10 is appropriately positioned, the device 12, which is configured as a hook 30 for grabbing a suture, wire, cable, or band, is then extended from the exit 20, by pushing the ring shaped handle 24. The suture, wire, cable, or band is then grabbed by the hook 30, and the ring shaped handle 24 is pulled, thereby retracting the hook 30 towards the exit 20. The bone cerclage tool 10 is then removed from the bone 14, and the suture, wire, cable, or band are pulled around the bone 14, thereby encircling the bone 14 and completing the bone cerclage procedure.

The device 12 adjoined to the resilient member 16 of the bone cerclage tool 10 may be configured as: the hook 30 for pulling a suture, wire, cable, or band around the bone 14; a saw for cutting the bone; a drill, router, screw driver, knife, or needle; spring fingers for grasping an object, or another appropriate implement for performing operations on or in the vicinity of the bone 14. The bone cerclage tool 10 is constructed of a sterilizable material, such as stainless steel or other suitable material.

Figure 2:
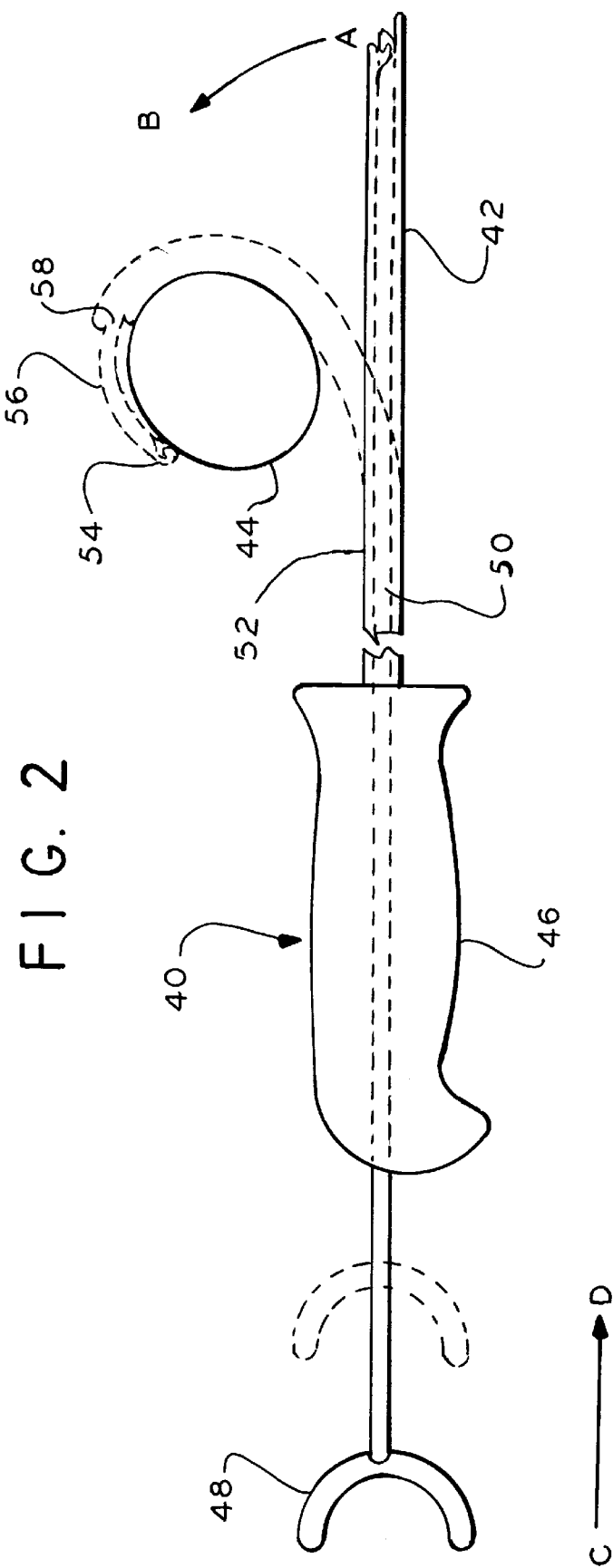
FIG. 2 is a side view of a bone cerclage tool which is another embodiment of the present invention.

An alternate embodiment of a bone cerclage tool 40 is shown in FIG. 2. A bendable tube 42 is provided for conformal shaping about a bone 44 and shaping for best access to an area where surgical procedures are to take place. The bendable tube 42 can be bent to a variety of curvatures, for use during orthopedic surgical procedures when very minimal access and/or visibility is available and the need for highly complex maneuvering around anatomical parts and different diameter bones is required. During surgical procedures the area in and around the vicinity of the bone 44 is prepared, and the bendable tube 42 of the bone cerclage tool 40 is bent to a shape conformal with the bone 44 and to allow for best access to and around the vicinity where surgical procedures are to be performed.

The bendable tube 42 is shown in an undeformed condition as A and in a bent condition as B, conformally shaped to the bone 44. A knife grip handle 46 is provided for holding the bone cerclage tool 40. A plunger handle 48 adjoined to a push-pull member 50 housed in a tube 52 is used to extend a device 54 and slidably abut the device 54 adjoined to a resilient member 56 against the bone 44. The plunger handle 48 is shown in a pulled condition as C and in a pushed condition as D.

The device 54 adjoined to the resilient member 56 is shown extended from the exit 58 about the bone 44 with the bendable tube 42 bent as in condition B and with the plunger handle 48 pushed as in condition D. The device 54 is shown retracted with the bendable tube 42 undeformed as in condition A and with the plunger handle 48 pulled as in condition C.

After being bent to the required shape, the bendable tube 42 is slidably abutted against the bone 44 with the device 54 retracted toward the exit 58. Next, after the bone cerclage tool 40 is appropriately positioned, the device 54 is then extended and directed from the exit 58, by pushing the plunger handle 48, such that the device 54 is slidably abutted against the bone 44. Surgical procedures, such as sawing the bone 44 or pulling a suture, are then performed on or in the vicinity of the bone 44 by repetitively pushing and pulling the plunger handle 48 back and forth. After completion of the surgical procedure the plunger handle 48 is pulled, thereby retracting the device 54 towards the exit 58. The bone cerclage tool 40 is then removed from the bone 44, completing the surgical procedure.

The bone cerclage tool 40 is constructed of a sterilizable material, such as stainless steel or other suitable material, with the bendable tube 42 of a sterilizable semi rigid material. The device 54 may be configured as: a hook for pulling the suture, wire, cable, or band around the bone 44; a saw for cutting the bone 44; a drill, router, screw driver, knife, or needle; means for grasping an object, such as spring fingers; or another appropriate implement for performing operations on or in the vicinity of the bone 44.

An alternate embodiment of a bone cerclage tool 60 shown in FIG. 3 is substantially the same as the bone cerclage tool 10 of FIG. 1, except that a curved tube 62, which can be configured into a variety of curvatures for conformally adapting to specific situations, is adjoined to a tube 64 for housing a push-pull member 66. A device 68 comprising a saw 70 and a hook 72 is adjoined to a resilient member 74. The saw 70 is conformally slidably abutted against a bone to be cut as the saw 70 is repeatedly extended and retracted from and to an exit section 76. A wire may be attached to the hook 72, in order to direct additional friction force to the bone being cut. A diverter 78 is provided for directing the resilient member 74 and the device 68 obliquely from the curved tube 62 and for directing the device 68 to conformally and proximately slidably abut against the bone. An alternative exit section 80 of the bone cerclage tool of FIG. 3 is shown in FIG. 3A. The exit section 80 is directed obliquely from a curved tube 82 for directing a device 84 to conformally and proximately slidably abut against a bone. The bone cerclage tool 60 is constructed of a sterilizable material, such as stainless steel or other suitable material. The device 68 of FIG. 3 and the device 84 of FIG. 3A may be configured with: the saw 70 and the hook 72 for sawing operations; or only with a hook for pulling suture, wire, cable, or band around the bone; only with a saw for cutting the bone; a drill, router, screw driver, knife, or needle; means for grasping an object, such as spring fingers; or another appropriate implement for performing operations on or in the vicinity of the bone.

Although the present invention has been described in considerable detail with reference to certain preferred versions thereof, other versions are possible.

Therefore, the spirit and scope of the appended claims should not be limited to the description of the preferred versions contained herein.

What is claimed is:

1. A bone cerclage tool consisting essentially of:
   (a) a tubular housing member having a proximate end and a distal end and being formed of a material selected to alone enable at least said distal end to be bendable to a variety of curvatures, said distal end having an exit opening formed therein;
   (b) a resilient member having an inner end and an outer end contained within the distal end of said tubular housing:
   (c) means to attach an orthopedic surgical device to the outer end of said resilient member;
   (d) means within said tubular housing for advancing and retracting said resilient member such that said resilient member is capable of being guided circumferentially bout a bone; and,
   (e) means to grip said tubular housing at its proximate end.

2. The cerclage tool of claim 1 wherein the distal end of said tubular housing is in the form of an arc of up to about 180 degrees with respect to the longitudinal axis of said tubular housing.

3. The cerclage tool of claim 1 wherein the distal end of said tubular housing is deformable through an arc of up to about 270 degrees.

4. The cerclage tool of claim 1 wherein said advancing and retracting means is a push-pull member.

5. The cerclage tool of claim 1 wherein said exit opening includes a diverter that enables said resilient member to be directed circumferentially obliquely about a bone while maintaining continuous contact with said bone.

6. The cerclage tool of claim 1 wherein said orthopedic surgical device is a hook.

7. The cerclage tool of claim 1 wherein said orthopedic surgical device is a saw.

8. The cerclage tool of claim 1 wherein said orthopedic surgical device is a knife.

9. The cerclage tool of claim 1 wherein said orthopedic surgical device is a tissue piercing means.

10. The cerclage tool of claim 1 wherein said orthopedic surgical device is a drill.

11. The cerclage tool of claim 1 wherein said orthopedic surgical device is a router.

12. The cerclage tool of claim 1 wherein said orthopedic surgical device is a screwdriver.

* * * * *